United States Patent [19]

Luijpers

[11] 4,418,701

[45] Dec. 6, 1983

[54] SYSTEM FOR DETERMINING THE VOLUME VALUE OF A CONFINED SPACE

[75] Inventor: Johannes G. T. Luijpers, Bunnik, Netherlands

[73] Assignee: Gould Medical B.V., Bilthoven, Netherlands

[21] Appl. No.: 185,552

[22] Filed: Sep. 9, 1980

[30] Foreign Application Priority Data

Sep. 14, 1979 [NL] Netherlands .................... 7906869

[51] Int. Cl.$^3$ .............................................. A61B 5/08
[52] U.S. Cl. ....................................... 128/729; 73/232
[58] Field of Search ............... 128/725, 727, 728, 729; 73/861.07, 861, 861.04, 232, 3, 1 G

[56] References Cited

U.S. PATENT DOCUMENTS

3,659,590 0/1972 Jones et al. ...................... 128/725
3,726,271 4/1973 Mondshine ....................... 73/861 X

FOREIGN PATENT DOCUMENTS

2912391 10/1980 Fed. Rep. of Germany ...... 128/727
6614445 4/1968 Netherlands ....................... 128/729
1252626 11/1971 United Kingdom ............... 128/729

OTHER PUBLICATIONS

Mostardi et al., Journal of Clin. Eng., vol. 4, No. 4, Oct.-Dec. 1979, pp. 347–351.

Primary Examiner—Kyle L. Howell
Assistant Examiner—John C. Hanley
Attorney, Agent, or Firm—Holman & Stern

[57] ABSTRACT

System for measuring the volume value of a confined space, in particular the functional residual capacity of the lungs of a patient, by means of a measuring space having a variable volume and a gas analyzer, which measuring space can be connected to the confined space and is provided with means for supplying and removing air, as well as for supplying oxygen and a detectable gas, the gas analyzer generating an output signal which is a linear function of the concentration of this detectable gas and the zero level of which is adjustable. The system having means allowing the output signal of the gas analyzer to be adjusted to zero before the detectable gas is supplied to the measuring space, an adjusting device allowing the output signal of the gas analyzer and a reference voltage to be equalized after the detectable gas has been supplied to the measuring space, and means which, after the measuring space has been brought into communication with the confined space, generate an output signal which corresponds to the volume value of the confined space and which is supplied to a display device.

12 Claims, 6 Drawing Figures

SYSTEM FOR DETERMINING THE VOLUME VALUE OF A CONFINED SPACE

BACKGROUND OF THE INVENTION

The invention relates to a system for measuring the volume value of a confined space, in particular the functional residual capacity of the lungs of a patient, by means of a measuring space having a variable volume and a gas analyzer, which measuring space can be connected to the confined space and is provided with means for supplying and removing air, as well as for supplying oxygen and a detectable gas, the gas analyzer generating an output signal which is a linear function of the concentration of this detectable gas and the zero level of which is adjustable.

With prior-art systems of this kind, it is necessary first to determine the so-called dead space of the measuring space before the volume value of the confined space can be measured, while the required volume is only available on the basis of a calculation. This makes the use of prior-art systems relatively awkward.

SUMMARY OF THE INVENTION

Accordingly, it is an object of the invention to provide a system of the type described, in which the above-mentioned drawback is obviated in a simple, but nevertheless effective manner.

To this end, the system according to the invention is characterized by means allowing the output signal of the gas analyzer to be adjusted to zero before the detectable gas is supplied to the measuring space; by an adjusting device allowing the output signal of the gas analyzer and a reference voltage to be equalized after the detectable gas has been supplied to the measuring space; and by means which, after the measuring space has been brought into communication with the confined space, generate an output signal which corresponds to the volume value of the confined space and which is supplied to a display service.

As a result, a system is obtained which allows the required volume value to be read directly from the display device without any auxiliary measurement being necessary.

According to a first embodiment, the adjusting device equalizes the output signal of the gas analyzer to the reference voltage, which has a constant value. The result attained in this manner is that the system determines the volume value of the confined space, irrespective of the dead volume of the measuring space, provided that a given, fixed quantity of the detectable gas is supplied to the measuring space. This embodiment is particularly suitable as a portable system to be used in combination with different measuring spaces.

According to an alternative embodiment of the invention, the adjusting device equalizes the reference voltage to the output signal of the gas analyzer. In this case, the result of measurement is independent of the amount of detectable gas supplied to the measuring space and/or of the sensitivity of the gas analyzer, provided that the variation in the dead volume of the measuring space remains within the permissible tolerances of the result of measurement. This embodiment is especially suitable when the system forms a permanent combination with a given measuring space, since in such case the requirements for the dead volume will usually be met.

BRIEF DESCRIPTION OF THE DRAWINGS

The invention will hereinafter be further explained with reference to the drawings, showing an embodiment of the invention.

DESCRIPTION OF A PREFERRED EMBODIMENT

Figure 1:
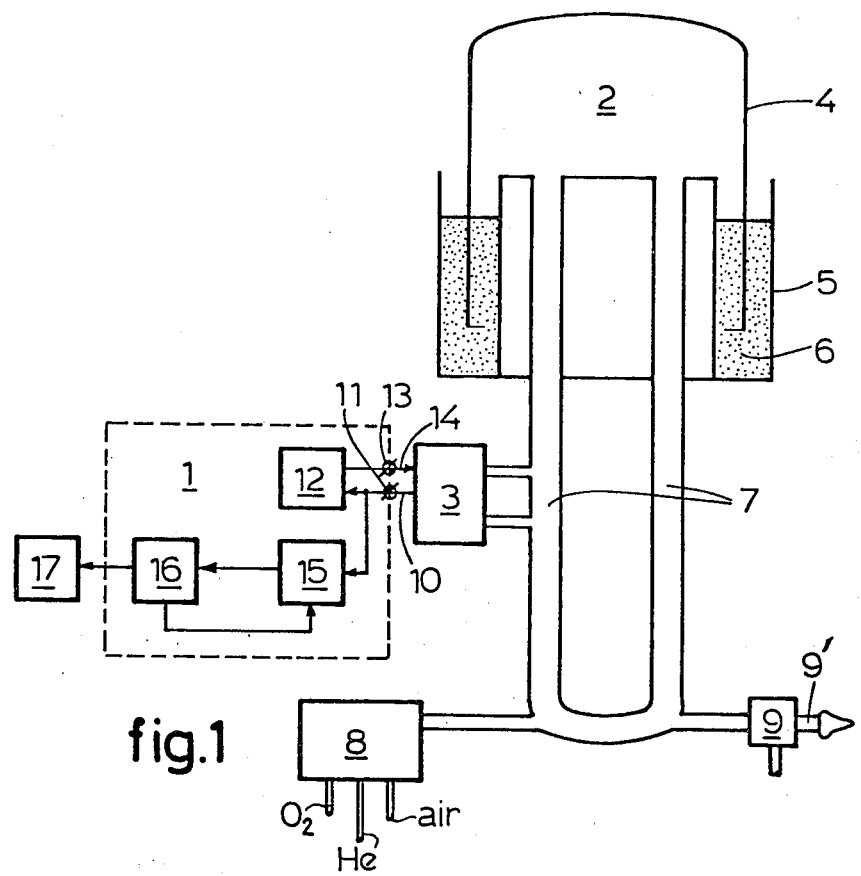
FIG. 1 shows a measuring arrangement in which use is made of an embodiment of the system according to the invention.

FIG. 1 shows a system 1 for measuring the functional residual capacity of a patient's lungs by means of a measuring space 2 and of a gas analyzer 3 connected with the measuring space 2. The volume of the measuring space 2 can be varied by raising or lowering a bell 4, which is vertically movable in a vessel 5. The vessel 5 is filled up to a certain level with a liquid 6, such as water, causing the space under the bell 4 to be shut off from the surroundings. The bell 4 is furthermore coupled in a usual manner to a device, not shown, by means of which the increase in volume of the measuring space 2 can be determined from the lowest level of the bell 4. The volume of the measuring space 2 in the lowest position of the bell 4 is usually called the dead volume.

The measuring space is accessible by way of a conduit 7, to which a valve system 8 is connected for supplying and removing air, for supplying oxygen, and for supplying a detectable gas, for which helium is preferably used in the embodiment described. The gas analyzer 3 is connected to the conduit 7, while a patient can likewise be connected to the conduit 7 with the use of a changeover valve 9. The changeover valve 9 possesses an input conduit 9' for the connection with the patient; in the one position it communicates with the atmosphere, and in the other position with the conduit 7. The conduit 7 accommodates a blower, not shown, with which a circulation of air can be induced in the measuring space 2. It is to be noted that the capacity of the various conduits which are connected to the measuring space 2 contributes to the overall volume of the measuring space 2.

The gas analyzer 3 produces an output signal at an output 10, which is connected to an input 11 of the system 1. Said output is dependent on the helium concentration inside the measuring space 2. The system 1 is equipped with means 12 with which the output signal of the gas analyzer 3 can be adjusted to zero before the helium is supplied to the measuring space 2. To this end, the means 12 produce a control signal at an output 13, which is connected to a control input 14 of the gas analyzer 3.

The input 11 of the system 1 is also connected to an adjusting device 15 which, after the helium has been supplied to the measuring space 2, equalizes the output signal of the gas analyzer 3 to a fixed reference voltage.

When the patient is connected with the measuring space 2, means 16 constitute an output signal which corresponds to the functional residual capacity of the patient's lungs and which is supplied to a display device 17. This measurement is based on the principle that if the gas analyzer 3 produces an output signal $V_{He1'}$ when a certain amount of air, oxygen and helium have been supplied to the measuring space 2, so that the volume of the measuring space is $V_1$, the helium concentration decreases after the patient has been connected, and the gas analyzer 3 will produce an output signal $V_{He2}$. The volume $V_x$ to be measured, which in this case is the functional residual capacity, is then given by:

$$V_1 V_{He1} = (V_1 + V_x) V_{He2}$$

$$V_x = V_1 \frac{V_{He1} - V_{He2}}{V_{He2}}$$

Figure 2A:
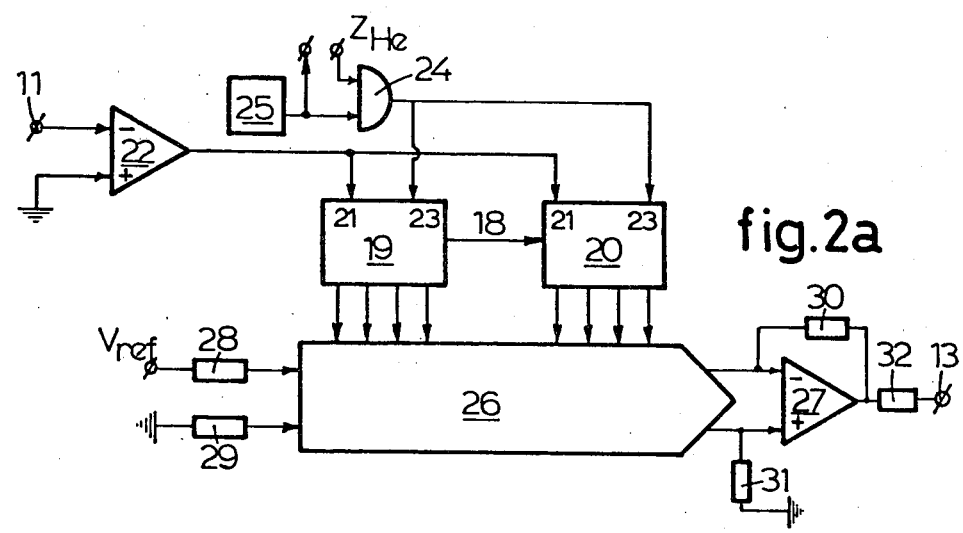
FIG. 2a is a schematic diagram showing the control signal generator circuit of the system of FIG. 1 in greater detail.
Figure 2B:
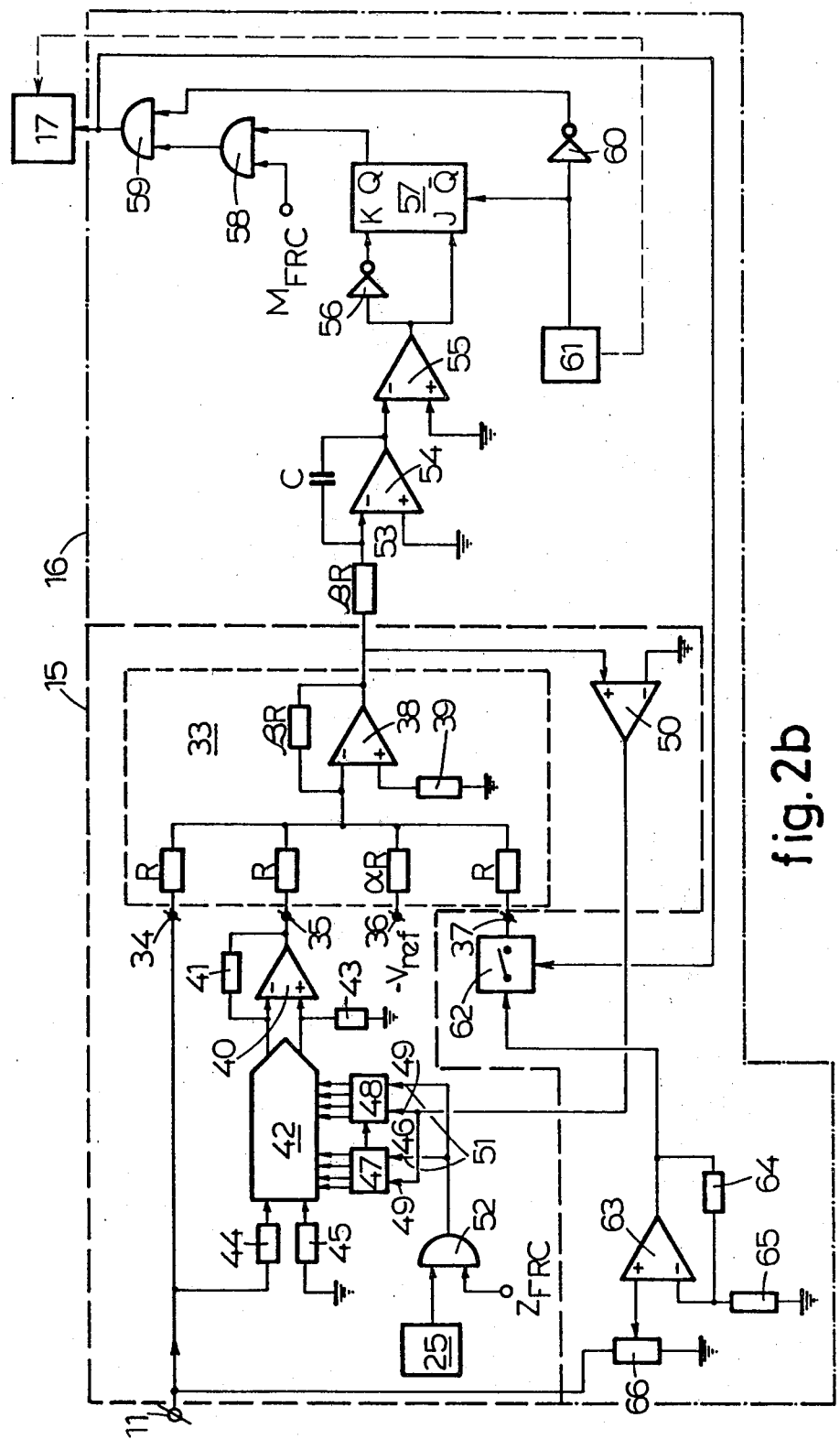
FIG. 2b is a schematic diagram showing the adjusting device circuitry and output signal circuitry of the system of FIG. 1 in greater detail.

FIGS. 2a and 2b show more detailed diagrams of the system 1, wherein all components required for supplying the feeding voltage and the like of the various parts are not shown. The means 12 are shown in greater detail in FIG. 2a and comprise a binary up-down counter 18 consisting of two counter stages 19 and 20 with 4 bits each, so that the counter 18 can count from 0 to 255. The counter stages 19 and 20 each possess a control input 21 for the counting direction, connected to the output of a comparator 22, a first, inverting input of which is connected to the input 11 of the system 1, and a second, non-inverting input being grounded. Clock inputs 23 of the two counter stages 19 and 20 are connected with the output of an AND gate 24, a first input of which is connected to a clock-signal source 25 which produces a block-wave signal of a suitable frequency, such as 10 c/s, and a second input of which receives a control signal $Z_{He}$, which indicates when the gas analyzer 3 must be adjusted to zero. When the control signal $Z_{He}$ has the logical value H (or "1"), the counter 18 receives the clock-signal, whereas, when the control signal $Z_{He}$ has the logical value L (or "0"), the clock-signal is not transmitted through the AND gate 24 and the count of the counter 18 is maintained.

The outputs of the counter 18, indicating the binary counter reading, are connected to the digital inputs of a digital-to-analog converter 26, the analog outputs of which are connected to the non-inverting and to the inverting input, respectively, of an operational amplifier 27. The reference inputs of the converter 26 are connected by resistors 28 and 29 to a positive reference voltage $V_{ref}$ and to the ground potential respectively. Feedback of the amplifier 27 is accomplished by means of a resistor 30, the non-inverting input being grounded by a resistor 31. The resistors 28 and 29 and the resistors 30 and 32 have identical values in pairs. Accordingly, the output of the amplifier 27 provides an analogue potential which is a function of the count of the counter 18 and which, by way of a resistor 32, is available at the output 13 for adjusting the output signal of the gas analyzer 3 to zero.

FIG. 2b shows details of the adjusting device 15 and of the means 16. A summing circuit 33 is equipped with four inputs 34, 35, 36 and 37, the inputs 34, 35 and 37 each being connected by a resistor having the value R and the input 36 by a resistor having the value $\alpha R$ to an inverting input of an operational amplifier 38 provided with a feedback resistor having the value $\beta R$. The non-inverting input of the amplifier 38 is grounded by way of a suitable resistor 39. The input 34 of the summing circuit 33 is connected to the input 11 of the system 1, the inputs 35 and 36 receiving, respectively, and adjustable voltage and a negative reference voltage $-V_{ref}$. The function of the input 37 will be discussed hereinafter.

The adjustable voltage is supplied by an operational amplifier 40, which is coupled back by means of a resistor 41 and of which an inverting and a non-inverting input are connected to respective analogue outputs of a digital-to-analog converter 42. The non-inverting input of the amplifier 40 is grounded by a resistor 43, which has the same value $R_1$ as the resistor 41. The reference inputs of the digital-to-analog converter 42 are connected by a resistor 44 to the input 11 and grounded by a resistor 45, respectively, both resistors having the resistance value $R_2$.

The digital inputs of the digital-to-analog converter 42 are connected to outputs of a binary up-down counter 46 which provide the binary count. The counter 46 consists of two counter stages 47 and 48 with four bits each, so that the counter 46 can count from 0 to 255. The counter stages 47 and 48 each possess a control input 49 for the counting direction and are connected to the output of a comparator 50, of which a first, non-inverting input is connected to the output of the amplifier 38 and of which a second, inverting input is grounded. The clock inputs 51 of the counter stages 47 and 48 are connected to the output of an AND gate 52, a first input of which is connected to the clock-signal source 25, which for the sake of clarity, is shown again in FIG. 2b. A second input of the AND gate 52 receives a control signal $Z_{FRC}$, which determines the transmission or non-transmission of the clock signal of the clock-signal source 25 to the clock input 51 of the counter stages 47 and 48.

When the control signal $Z_{FRC}$ has the logical value H, the output signal of the amplifier 38 is equalized to zero as a result of the output signal of the gas analyzer 3 being equalized to the reference voltage ($V_{ref}/\alpha$), at which the counter 46 will reach a given count. The count of the counter 46 is maintained when the control signal $Z_{FRC}$ returns to the logical value L.

The output of the amplifier 38 is furthermore connected to an input of an integrator 53, comprising an operational amplifier 54, a capacitor C and a resistor having the value $\beta R$. The output of the integrator 53 is connected to a negative input of a comparator 55, a positive input of which is again grounded. The output of the comparator 55 is connected directly to a J-input and, by an inverter 56, to a K-input of a JK flip-flop 57. A non-inverting output Q of the flip-flop 57 is connected to a first input of an AND gate 58, a second input of which receives a control signal $M_{RFC}$, so that the signal of the output Q of the flip-flop 57 appears at the output of the AND gate 58 when the control signal $M_{FRC}$ has the logical value H. The output of the AND gate 58, however, always has the logical value L when the control signal $M_{FRC}$ has the logical value L. The control signal $M_{FRC}$ determines when a measurement will be performed.

The output of the AND gate 58 is connected to a first input of an AND gate 59, a second input of which receives a clock signal, inverted by an inverter 60 and provided by a clock signal source 61 which is connected directly to a clock input of the JK flip-flop 57. The output of the AND gate 59 is connected to a control input of a switching element 62, an output of which is connected to the input 37 of the summing circuit 33. An input of the switching element 62, which in the closed position is interconnected with the output, is connected to the output of an operational amplifier 63, the amplification of which is determined by means of resistors 64 and 65. The non-inverting input of the amplifier 63 is connected to a wiper of a potentiometer 66, one side of which is grounded and the other side of which is connected to the input 11 of the system 1. In the closed position of the switching element 62, the input 37 of the summing circuit 33 is, therefore, provided with a part of the output voltage of the gas analyzer 3 which is adjustable by means of the potentiometer 66.

The operation of the system is as follows:

Prior to performing a measurement, the measuring space 2 is scavenged, for instance by raising and lowering the bell 4 a number of times, with the measuring space 2 communicating with the atmosphere through the valve system 8. At this time, the measuring space 2 contains air only, and the output signal of the gas analyzer 3 must be set at zero. To this end, the control signal $Z_{He}$ receives the logical signal H, and the counter 18, under the control of the clock-signal source 25, can start counting, with the comparator 22 determining the counting direction. As a result, a count is obtained at which the output voltage of the gas analyzer 3, hereinafter referred to with $g_1V_{He}$, is at least substantially equal to zero. The control signal $Z_{He}$ then returns to the logical value L.

Air, oxygen and a fixed amount of helium are then introduced through the valve system 8 into the measuring space 2, whereupon the output signal $g_1V_{He1}$ at the input 11 of the system 1 is equalized to the reference voltage $(-V_{ref}/\alpha)$ by means of the digital-to-analog converter 42 and the counter 46. The control signal $Z_{FRC}$ then assumes the value H, so that the counter 46 receives the clock-signal of the clock-signal source 25.

The signal at the input 35 of the summation circuit 33 is given by:

$$V_{i35} = \frac{g_1 V_{He1}}{R_2} \cdot \frac{T-128}{128} \cdot R_1,$$

where T is the count of the counter 46 ($0 \leq T \leq 255$).

Since the control signal $M_{FRC}$ has the value L, the switching element 62 is not closed, so that there is no signal at the input 37. When the counter 46, under the control of the clock-signal source 25 and the comparator 50, has reached a count at which the output voltage of the summing circuit 33 is at least substantially equal to zero, we have:

$$\left( g_1 V_{He1} + \frac{g_1 V_{He1}}{R_2} \cdot \frac{T-128}{128} \cdot R_1 \right) \frac{1}{R} = \frac{V_{ref}}{\alpha R};$$

$$g_1 V_{He1} \left( 1 + \frac{R_1}{R_2} \cdot \frac{T-128}{128} \right) = \frac{V_{ref}}{\alpha}.$$

The output signal $g_1V_{He1}$ of the gas analyzer 3 has now been equalized to a constant reference voltage $(V_{ref}/\alpha)$.

Assuming that $$g_1 \left( 1 + \frac{R_1}{R_2} \cdot \frac{T-128}{128} \right) = g_2,$$

we have:

$$g_2 V_{He1} = \frac{V_{ref}}{\alpha}.$$

The factor $g_2$ here compensates any possible variation in the volume of the measuring space 2. The ratio of resistances $R_1/R_2$ determines the extent to which $g_1V_{He1}$ can be adjusted, as well as, together with the smallest step of the counter 46, the accuracy with which the adjustment takes place.

The control signal $Z_{FRC}$ now returns to the value L, so that the count of the counter 46 and, therefore, the factor $g_2$ are maintained.

The patient can now be connected to the measuring space 2, wherein the control signal $M_{FRC}$ goes to the value H. As a result, the helium concentration will decrease, so that the output voltage of the summing circuit 33 becomes positive. The integrator 53 then starts integrating downwards, causing the inputs J and K of the flip-flop 57, through the comparator 55, to become equal to 1 and 0, so that the output Q, under the control of the clock signal source 61 with clock signal $f_{in}$, assumes the value H.

As a result, an output signal $f_0$ appears at the output of the AND gate 59, causing the switching element 62 to receive a control signal and to be closed. A further positive signal $g_1g_3V_{He2}$ appears at the input 37 of the summing circuit 33, $g_3$ being determined by the setting of the potentiometer 66.

The output voltage of the summing circuit 33 becomes negative and the integrator 53 starts integrating upwards, so that the output Q of the flip-flop 57 goes to the value L. In the equilibrium state, the output voltage of the integrator 53 varies around zero, with:

$$\frac{-V_{ref}}{\alpha} + g_2 V_{He2} + g_1 g_3 V_{He2} \cdot f_0 \cdot \frac{1}{2f_{in}} = 0;$$

$$f_o = \frac{2f_{in}}{g_1 g_3 V_{He2}} \left( \frac{V_{ref}}{\alpha} - g_2 V_{He2} \right).$$

$(V_{ref}/\alpha)$ is given by:

$$\frac{V_{ref}}{\alpha} = g_2 V_{He1},$$

so that $$f_o = 2f_{in} \frac{g_2}{g_1 g_3} \left( \frac{V_{He1} - V_{He2}}{V_{He1}} \right). \tag{1}$$

It follows from the above equation (1) that the output signal of the AND gate 59 corresponds to the functional residual capacity to be measured. The potentiometer 66 allows the system 1 to be properly calibrated by changing the factor $g_3$. The system 1, having been calibrated once, from then allows the functional residual capacity to be measured irrespective of the dead volume of the measuring space 2.

Figure 3:
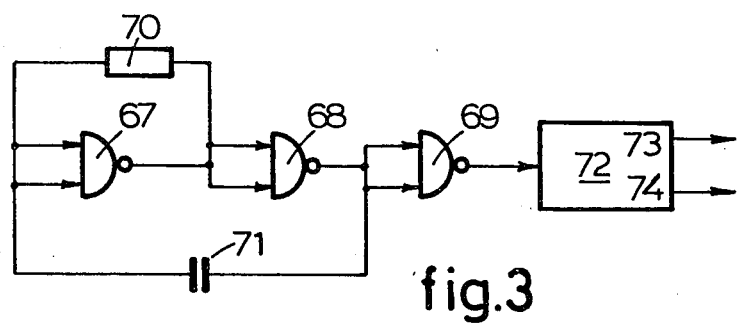
FIG. 3 is a diagram of the second clock-signal source shown in FIG. 2b.

The dependence of the output signal $f_o$ from $f_{in}$ which output signal $f_o$ is supplied to the display device 17, can be eliminated in a simple manner by measuring the output signal $f_o$ during a period which is inversely proportional to the frequency of the clock signal $f_{in}$. For this purpose, the embodiment of the clock signal source 61 shown in FIG. 3 could, for example, be used.

The clock signal source 61 is equipped with three series-connected NAND gates 67, 68 and 69, a resistor 70 and a capacitor 71. The resistor 70 and the capacitor 71 determine the frequency f of the oscillator obtained. The output of the NAND gate 69 is connected to a clock input of a divider circuit 72 having two outputs 73 and 74, respectively producing the clock signal $f_{in}$ and a signal $f_w$ for the control of the display device 17, with $f_{in}=(f/2^{n1})$ and $f_w=(f/2^{n2})$.

Figure 4:
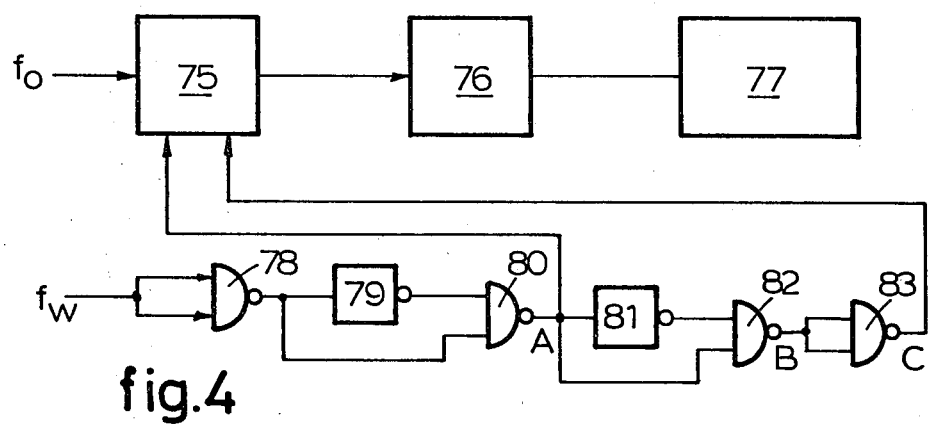
FIG. 4 is a diagram of the display device used with the system according to FIG. 1.
Figure 5:
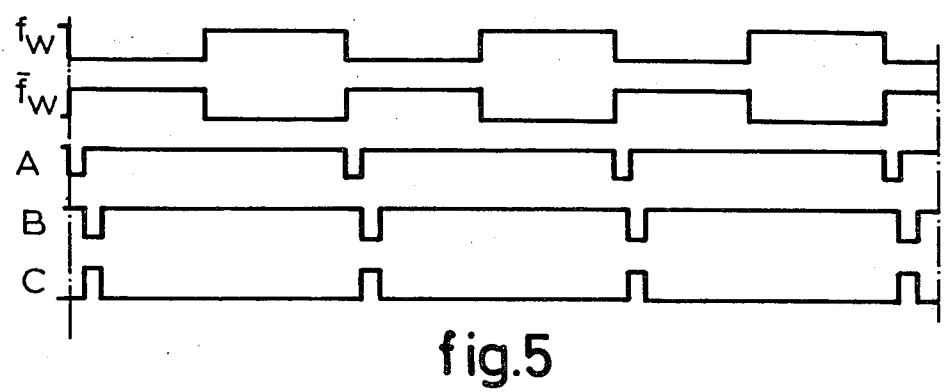
FIG. 5 is a diagram showing a number of signals used with the display device according to FIG. 4.

The display device 17 is shown in FIG. 4 and comprises a counter means 75 with a memory, and a decoding means 76 which converts the output signal of the counter means 75 into a suitable signal for operating a seven-segment display device 77. The signal $f_w$ of the output 74 of the clock signal source 61 is supplied to both inputs of a NAND gate 78, the output of which is connected directly to a first input and by way of an inverting delay 79 to a second input of a NAND gate 80. The output of the NAND gate 80 is again connected directly to a first input and by way of an inverting delay 81 to a second input of a NAND gate 82, the output of which is connected to both inputs of a NAND gate 83. The signals A, B and C thus obtained are shown together with the signal $f_w$ in FIG. 5.

The signal A is used as activating signal for the memory of the counter means 75, the signal C being used as reset signal for the counter means 75. The counter means 75 counts the number of impulses of the output signal $f_o$ of the AND gate 59 occurring between the trailing edge of an impulse of the signal C and a trailing edge of an impulse of the signal A, i.e., during a period of $1/f_w$.

The display device 77 then displays:

$$\frac{f_o}{f_w} = 2 \cdot \frac{2^{n2}}{2^{n1}} \cdot \frac{g_2}{g_1 g_3} \cdot \frac{V_{He1} - V_{He2}}{V_{He2}},$$

which is not dependent on the frequency $f_{in}$.

As an alternative for the system 1 described hereinabove, the one reference input of the digital-to-analog converter 42 connected by the resistor 44 to the input 11, can be connected by the resistor 44 to a positive reference voltage $V_{ref1}$. In this case, $g_1 V_{He1}$ is not equalized to the voltage $(V_{ref}/\alpha)$, but said voltage now is adjusted to $g_1 V_{He1}$, with $$\left( g_1 V_{He1} + \frac{V_{ref1}}{R_2} \cdot \frac{T - 128}{128} \cdot R_1 \right) \frac{1}{R} = \frac{V_{ref}}{\alpha R};$$

$$g_1 V_{He1} = \frac{V_{ref}}{\alpha} - \frac{V_{ref1}}{R_2} \cdot \frac{T - 128}{128} R_1.$$

After the patient has been connected, when the control signal $M_{FRC}$ assumes the value H and the equilibrium state is reached, this leads to:

(2)

$$\frac{-V_{ref}}{\alpha} + \frac{V_{ref1}}{R_2} \cdot \frac{T - 128}{128} \cdot R_1 + g_1 V_{He2} + g_3 g_1 V_{He2} \cdot \frac{f_o}{2 f_{in}} = 0;$$

$$f_o = \frac{2 f_{in}}{g_3} \left( \frac{V_{He1} - V_{He2}}{V_{He2}} \right).$$

Comparison of the above equation (2) with the equation (1) shows that the factor $g_1$, indicating the sensitivity of the gas analyzer 3 and/or the amount of helium supplied to the measuring space 2, has been eliminated, so that the measuring result has become independent of these parameters. On the other hand, the compensation of $g_1 V_{He1}$ by means of the factor $g_2$ is no longer available, so that the measuring result can now vary with the dead volume of the measuring space 2. This, however, is not objectionable in the case of a measuring arrangement in which the system 1 is operated permanently with the same measuring space 2, since any variation of the dead volume then falls within the permissible tolerances of the measuring result.

The control signals $Z_{He}$, $Z_{FRC}$ and $M_{FRC}$ may be provided, for example, by a control unit, not shown, which may comprise a microprocessor.

For a simpler embodiment of the system according to the invention, the circuit shown in FIG. 2a could be replaced, if desired, by an adjusting potentiometer, the wiper of which is connected to the output 13. In such case, a measuring device should be present allowing the output signal of the gas analyzer 3 to be read off. In the circuit shown in FIG. 2b, components 40–46, 25 and 52 could be similarly replaced by an adjusting potentiometer, the wiper of which is connected to the input 35 of the summing circuit 33. The output voltage of the summing circuit should then likewise be capable of being read off at the measuring device.

Accordingly, the invention is not restricted to the embodiment described hereinabove, which can be varied in a number of manners within the scope of the invention.

What is claimed is:

1. A system for measuring the volume of a confined space, in particular the functional residual capacity of the lungs of a patient, said system being of the type which includes a measuring space having a variable volume, means for selectively connecting the measuring space to the confined space, means for supplying air to and removing air from as well as for supplying oxygen and a detectable gas to the measuring space, a gas analyzer for generating an output signal which is a linear function of the concentration of the detectable gas and which has an adjustable zero level, said system further comprising:

output adjustment means for selectively adjusting to zero the output signal of the gas analyzer before the detectable gas is supplied to the measuring space;

an adjusting device for equalizing the output signal of the gas analyzer with a reference voltage after the detectable gas has been supplied to the measuring space, said adjusting device being provided with a summing circuit, a first input of which is connected to the output of the gas analyzer, a second input of which is connected to the reference voltage and a third input of which is connected to an adjustable voltage, and output of the summing circuit being adjustable to zero by adjusting the adjustable voltage;

means for generating a system output signal after the measuring space has been brought into communication with the confined space, said generating means comprising an adjustable voltage divider connected to the output of the gas analyzer and providing an adjustable portion of the output signal of the gas analyzer to a fourth input of the summing circuit by means of an electrically switching element;

a display device connected to receive said output signal.

2. A system according to claim 1, further comprising a digital-to-analog converter for providing said adjustable voltage, a first binary up-down counter providing binary outputs and having a clock input, and a first clock signal source for providing a first clock signal, wherein said digital-to-analog converter includes binary inputs which are connected to count the binary output of said first binary up-down counter, and wherein the clock input of said first binary up-down counter is connected to receive said first clock signal from said first clock signal source, a comparator having a first input and a second input, means connecting the output signal from said summing circuit to said first input of said comparator, means connecting the second input of said comparator to ground, wherein said first binary up-down counter includes a control input for controlling counting direction, wherein said comparator has an output connected to said control input of said first up-down binary counter, wherein said digital-to-analog converter includes a reference input connected to the output of said gas analyzer, and means for providing said adjustable voltage as a function of the voltage connected to said reference input of said digital-to-analog converter.

3. A system according to claim 1, further comprising a digital-to-analog converter for providing said adjustable voltage, a first binary up-down counter providing binary outputs and having a clock input, and a first clock signal source for providing a first clock signal, wherein said digital-to-analog converter includes binary inputs which are connected to count the binary output of said first binary up-down counter, and wherein the clock input of said first binary up-down counter is connected to receive said first clock signal from said first clock signal source, a comparator having a first input and a second input, means connecting the output signal from said summing circuit to said first input of said comparator, means connecting the second input of said comparator to ground, wherein said first binary up-down counter includes a control input for controlling counting direction, wherein said comparator has an output connected to said control input of said first up-down binary counter, wherein said digital-to-analog converter includes a reference input connected to a positive reference voltage, and means for providing said adjustable voltage as a function of the voltage connected to said reference input of said digital-to-analog converter.

4. A system according to claim 2 or 3, wherein the output of the summing circuit is connected to an integrator, an output of which is connected to a first input of a second comparator, a second input of said second comparator being grounded and an output of said second comparator being coupled to a first input of an AND gate, another input of which is connected to a second clock signal source, said switching element being controlled by an output of the AND gate, in such a manner that the output signal of said AND gate corresponds to the volume value of the confined space.

5. System according to claim 4, wherein the output of the second comparator is connected directly to the J-input and by way of an inverter to the K-input of a JK flip-flop, one output of which is coupled to the first input of the AND gate, the second clock-signal source being connected by way of an inverter to the second input of the AND gate and directly to a clock input of the JK flip-flop.

6. System according to claim 5, wherein the output of the JK flip-flop is connected to a first input of a second AND gate, an output of which is connected to the first input of the first AND gate, a second input of the second AND gate receiving a control signal which enables this second AND gate when the space to be measured is connected with the measuring space.

7. System according to claim 6, wherein the output of the gas analyzer is connected by means of an adjustable voltage divider to an input of an amplifier, the output of which is connected to the controllable switching element.

8. System according to claim 7, wherein the means for the adjustment to zero of the output signal of the gas analyzer comprise a second binary up-down counter, a clock input of which is coupled to the first clock signal source, and a digital-to-analog converter, binary inputs of which are connected to count outputs of the counter, the analogue output of the converter being coupled to a control input of the gas analyzer for the adjustment to zero of the output signal, said output of the gas analyzer being connected to a first input of a comparator, a second input of which is grounded and an output of which is connected to a control input for the counting direction of the counter.

9. System according to claim 8, wherein the first clock signal source is connected to a first input of a third AND gate, an output of which is connected to the clock input of the second counter, a second input of said third AND gate receiving a control signal with which the AND gate can be disabled.

10. System according to claim 9, wherein the first clock signal source is connected to a first input of a fourth AND gate, an output of which is connected to the clock input of the first counter, a second input of said fourth AND gate receiving a control signal with which the AND gate can be disabled.

11. System according to claim 10, wherein the display device comprises a counter means, the count of which reached during a given measuring period is displayed by the display device.

12. System according to claim 11, wherein the second clock signal source has two outputs, the frequencies of the output signals differing by a factor $2^n$, the first output being connected by way of the inverter to the aforementioned input of the first AND gate, while the second output controls the measuring period of the display device.

* * * * *